US006251583B1

(12) United States Patent
Zhang et al.

(10) Patent No.: US 6,251,583 B1
(45) Date of Patent: Jun. 26, 2001

(54) PEPTIDE SUBSTRATES FOR HCV NS3 PROTEASE ASSAYS

(75) Inventors: Rumin Zhang, Edison; Bruce A. Malcolm, Westfield; Brian M. Beyer, Summit; F. George Njoroge, Union; James P. Durkin, Succasunna; William T. Windsor, East Brunswick, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/288,391

(22) Filed: Apr. 8, 1999

Related U.S. Application Data

(60) Provisional application No. 60/083,204, filed on Apr. 27, 1998.

(51) Int. Cl.[7] .............................. C12Q 1/70; C12Q 1/37; C07K 7/06; C07K 7/08; C07K 7/02
(52) U.S. Cl. ............................... 435/5; 435/23; 530/324; 530/326; 530/327; 530/328; 530/329; 530/332
(58) Field of Search ................................... 435/5, 23, 24, 435/212, 219; 530/326, 327, 323, 332, 324, 328, 329

(56) References Cited

U.S. PATENT DOCUMENTS

| 5,861,297 | * | 1/1999 | Sardana et al. ....................... 435/219 |
| 6,037,137 | * | 3/2000 | Komoriya et al. ..................... 435/23 |

FOREIGN PATENT DOCUMENTS

| WO 95/22985 | | 8/1995 | (WO). |
| 96/35717 | * | 11/1996 | (WO) ............................. C07K/14/18 WO/ |
| 97/04097 | | 2/1997 | (WO). |
| 97/19103 | * | 5/1997 | (WO) .............................. C07K/7/06 |
| WO 99/14240 | | 3/1999 | (WO). |

OTHER PUBLICATIONS

Krafft et al (Methods in Enzymology 241:70–86, 1994).*
Landro, James A., et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping," Biochemistry, 1997, 36:9340–9348.
de Jersey, John, et al., "Oxazolinone Intermediates in the Hydrolysis of Activated N–Acylamino Acid Esters. The Relevance of Oxazolinones to the Mechanism of Action of Serine Proteinases," Biochemistry, 1969, 8:5 pp. 1959–1967.
Schade, Sylvia Z., et al., "BODIPY–α–Casein, a pH–Independent Protein Substrate for Protease Assays Using Fluorescence Polarization," Analytical Biochemistry, 1996, 243:1–7.

Jolley, Michael E., "Fluorescence Polarization Assays for the Detection of Proteases and their Inhibitors," Journal of Biomolecular Screening, 1996, 1:1 pp. 33–88.
Levine, Leanna M., et al., "Measurement of Specific Protease Activity Utilizing Fluorescence Polarization," Analytical Biochemistry, 1997, 247:83–88.
Levitskaya, Jelena, et al., "Inhibition of Antigen Processing by the Internal Repeat Region of the Epstein–Barr Virus Nuclear Antigen–1," 1996, Nature, 375:685–688.
Williams, Andres, The Oxazolinone Intermediate in the Hydrolysis and Aminolysis of N–Benzoylglycine Derivatives, J. Chem. Soc., Perkin Trans. 2 (1975) (9) 947–953.
Takeshita, Norisue, "An Engyme–Lined Immunosorbent Assay for Detecting Proteolytic Activity of Hepatitis C Virus Proteinase," Analytical Biochemistry, 1997, 247:242–246.
Taliani, Marina, et al., "A Continuous Assay of Hepatitis C Virus Protease Based on Resonance Energy Transfer Depsipeptide Substrates," Analytical Biochemistry, 1996, 240:60–67.
Bianchi, Elisabetta, et al., "Synthtic Depsipeptide Substrates for the Assay of Human Hepatitis C Virus Protease," Analytical Biochemistry, 1996, 237: 239–244.
Bouffard, Pascal, et al., "An in Vitro Assay for Heptaitis C Virus NS3 Serine Proteinase," Virology, 1995, 209:52–59.
Lin, Chao, et al., "The Hepatitis C Virus NS3 Serine Proteinase and NS4A cofactor: Establishment of a cell–free trans–processing Assay," Proc. Natl. Acad. Sci. USA 92:7622–7626.
Tartour, E., et al., "IL17, a T cell derived cytokine which promotes the in vivo growth of cervicall tumors in nude mice,"1998, 39:3 No. 4447 p. 653, Abstract.
Laan, Martti, et al., "Neutrohil Recruitment by Human IL–17 Via C–X–C Chemokine Release in the Airways," 1999, The Journal of Immunology, pp. 2347–52.
Antonysamy, Mary A., et al., "Evidence for a Role of IL–17 in Organ Allograft Rejection: IL–17 Promotes the Functional Differentiation of Dendirtic Cell Progenitors," 1996, The Journal of Immunology, pp. 577–84.
Fossiez, Francois et al., Interleukin–17, 1998, Immunol, 16:541–551.
Pages, Franck et al., "Control of tumor development by intratumoral cytokines," 1999, Immunology letters 68:135, 139.
Tartour, Eric, et al., "Interleukin 17, a T–cell–derived Cytokine, Promotes Tumorgenicity of Human Cervical Itumors in Nude Mice," 1999, Cancer Research 59:3698–3704.
Spriggs, Melanie K., "Interleukin–17 and Its Receptor," Journal of Clinical Immunology, 17:5 1997.
Yao, Zhengbin et al., "Human IL–17: A Novel Cytokine Derived from T Cells," The Journal of Immunology, 1995, 155:5483–5486.

* cited by examiner

*Primary Examiner*—Mary E. Mosher
(74) *Attorney, Agent, or Firm*—Richard J. Grochala; Christine F. Martin

(57) ABSTRACT

Novel chromogenic, fluorogenic and fluorescence polarization substrates which are useful in HCV NS3 protease and inhibitor assays.

32 Claims, No Drawings

PEPTIDE SUBSTRATES FOR HCV NS3 PROTEASE ASSAYS

This application claims priority to provisional application serial no. 60/083204, filed on Apr. 27, 1998.

BACKGROUND OF THE INVENTION

Hepatitis C virus (HCV) accounts for greater than 90% of transfusion-associated hepatitis in the U.S. and it is the predominant form of hepatitis in adults over 40 years of age. Almost all of the infections result in chronic hepatitis and nearly 20% of those infected develop liver cirrhosis.

Molecular cloning of the HCV genome has been accomplished by isolating the messenger RNA (mRNA) from the serum of infected chimpanzees and preparing cDNA using recombinant methodologies. [Grakoui A. et al., 1993, J. Virol. 67: 1385–1395]. It is now known that HCV contains a positive strand RNA genome comprising approximately 9400 nucleotides, organization of which is similar to that of flaviviruses and pestiviruses. The genome of HCV, a (+)-stranded RNA molecule of ~9.4 kb, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least ten mature viral proteins are produced from the polyprotein by specific proteolysis. The order and nomenclature of the cleavage products are as follows: $NH_2$-C-E1-E2-p7-NS2-NS3-NS4A-NS4B-NS5A-NS5B-COOH [Grakoui et al., 1993, J. Virol. 67:1385–95; Hijikata et al., 1991, PNAS 88:5547–51; Lin et al., 1994, J. Virol. 68:5063–73]. The three amino-terminal putative structural proteins, C (capsid), E1, and E2 (two envelope glycoproteins), are believed to be cleaved by a host signal peptidase of the endoplasmic reticulum (ER). The host enzyme is also responsible for generating the amino terminus of NS2. The proteolytic processing of the nonstructural proteins are carried out by the viral proteases: NS2-3and NS3, contained within the viral polyprotein. The NS2-3 protease catalyzes the cleavage between NS2 and NS3. It is a metalloprotease and requires both NS2 and the protease domain of NS3.

The NS3 protease catalyzes the rest of the cleavages in the nonstructural part of the polyprotein. The NS3 protein contains 631 amino acid residues and is comprised of two enzymatic activities: the protease domain contained within amino acid residues 1–181 and a helicase AIPase domain contained within the rest of the protein [Kim et al., 1995, Biochem Biophys Res. Comm., 215:160–166]. The gene encoding the HCV NS3 protein has been cloned as disclosed in U.S. Pat. No. 5,371,017. The NS3 protease is a member of the serine class of enzymes using a His, Asp, Ser catalytic triad [Love et al., 1996, Cell 87:331–42; Kim et al., 1996, Cell 87:343–55; Yan et al., 1998, Protein Science 7:83747]. Mutation of the Ser residue abolishes cleavage of NS3/4A, NS4A/4B, NS4B/5A, and NS5A/5B substrates. The cleavage between NS3 and NS4A is intramolecular, whereas the cleavages at the NS4A/4B, 4B/5A,5A/5B sites occur in trans.

Experiments using transient expression of various forms of HCV NS polyproteins in mammalian cells have established that the NS3 serine protease is necessary but not sufficient for efficient processing of all of these cleavages. Efficient proteolytic processing at NS4A/4B, NS4B/5A, and NS5A/5B sites within the non-structural domain of hepatitis C virus requires a heterodimeric complex of the NS3 serine protease and the NS4A protein. [Bartenschlager et al. 1995J. Virol. 67:3835–3844; Failla et al., 1994, J. Virol. 68:3753–3760]. Smaller domains of the NS4A protein have been shown to be sufficient for activation of NS3 protease [Butkiewicz et al., 1996, Virology, 225: 328–338; Lin et al., 1995, J. Virol 69:4377–8].

Because the HCV NS3 protease cleaves the non-structural HCV proteins necessary for HCV replication, the NS3 protease can be a target for the development of therapeutic agents against the HCV virus. Numerous medium to high throughput assays have been developed for the purpose of detecting inhibitors of HCV NS3 protease.

One example of such an assay that can be used to discover NS3 protease inhibitors is the scintillation proximity assay (SPA). SPA technology involves the use of beads coated with scintillant. Bound to the beads are acceptor molecules such as antibodies, receptors or enzyme substrates which interact with ligands or enzymes in a reversible manner. In a typical protease assay, the substrate peptide is biotinylated at one end and the other end is radiolabelled with low energy emitters such as $^{125}I$ or $^{3}H$. The labeled substrate is then incubated with the enzyme. Avidin coated SPA beads are then added which bind to the biotin. When the substrate peptide is cleaved by the protease, the radioactive emitter is no longer in proximity to the scintillant bead and no light emission takes place. Inhibitors of the protease will leave the substrate intact and can be identified by the resulting light emission which takes place in their presence.

Another type of assay which can be used to screen for and characterize protease inhibitors are those that involve the use of substrates containing chromophores or fluorophores to detect cleavage. In a typical assay, a peptide substrate is attached to a chromophore or fluorophore and brought into contact with a protease known to cleave the substrate. The chromophore or fluorophore is released upon cleavage by the protease, and gives rise to an increase in absorbance or fluorescence detectable continuously or at assay's end-point by a commercial spectrophotometer or spectrofluorometer at certain wavelengths characteristic of the free chromophore or fluorophore. Alternatively, fluorescence can be detected from a substrate in which the effect of a fluorescent acceptor (resonance energy transfer) or quencher car. be released upon protease cleavage.

Another type of assay useful in detecting and characterizing protease inhibitors is the fluorescence polarization assay [see, e.g., Jolley et al., 1996, Journal of Biomolecular Screening 1(1):33–381]. In this type of assay, a substrate comprising both P and P' regions of the protease cleavage site is attached to a high molecular weight (MW) molecule binding moiety at one end, and a fluorophore molecule at the other end. Cleavage by the protease results in the separation of the side to which the high molecular weight binding site has been attached from the side to which the fluorophore molecule has been attached. Upon addition of a high molecular weight molecule which will bind to the high MW molecule binding moiety, the overall fluorescence polarization will decrease compared to that of no cleavage or an inhibited reaction. This method tolerates compounds that absorb light in the excitation and/or emission wavelength regions of the fluorophore.

A number of different chromogenic substrates are known. For example, para-nitroanilide (pNA) based substrates are widely known and used in various protease assays. HCV NS3 peptide substrates containing pNA have also been published [Landro et al., 1997, *Biochemistry* 36:9340–48; WO 97/19103], and made commercially available [Ac-EEVVAC-pNA from BACHEM]. Nitrophenyl esters have also been used to investigate the mechanism of action of serine proteases [e.g. Jersey et al., 1969, *Biochemistry* 8(5):1959–66; Williams, 1975, *Journal of Chemical Society Perkin II*, 947–53].

There are also a number of publications on the use of fluorogenic substrates in HCV assays. For example, WO 97/08194 and WO 9719103 disclose fluorescent substrates for hepatitis C virus NS3 serine protease assays that are derived from amine containing fluorophores. Resonance energy transfer (e.g., DABCYL/EDANS) based fluorescent substrates and 7-amido-4-methylcoumarin (AMC) based fluorogenic substrate are commercially available (BACHEM).

Substrates have also been reported for use in fluorescence polarization assays to detect both viral and non-viral proteases and their inhibitors [jolley et al., 1996, *Journal of Biomolecular Screening* 1(1):33–38; Levine et al., 1997, *Analytical Biochemistry* 247:83–88; Schade et al ., 1996, *Analytical Biochemistry* 243:1–7].

Known chromogenic and fluorogenic substrates, however, lack the sensitivity and/or cleavability necessary for an optimal HCV NS3 protease assay. Since HCV NS3 protease has its distinct substrate specificity [e.g., see Urbani et al, 1997, *Journal of Biological Chemistry*, 272(14):9204–9209; Zhang et al, 1997, *Journal of Virology*, 71(8): 6208–6213; Kakiuchi et al, 1997, *Journal of Biochemistry*, 122: 749–755], the pNA-based chromogenic substrates and AMC-based fluorogenic substrates for HCV NS3 protease, in contrast to similar types of substrates for other proteases, turned out to be very inefficiently cleaved, requiring long reaction time and large quantities of the protease to generate weakly detectable signals. No fluorescence polarization based substrates for HCV NS3 protease have been reported.

In order for a chromogenic, fluorogenic or fluorescence polarization substrate to be practically useful in assays which monitor single end-point or continuous inhibition kinetics and provide rapid characterization of HCV NS3 protease inhibitors, there is a need for the substrates to be highly sensitive and deavable and have high specificity for the HCV NS3 protease.

SUMMARY OF THE INVETION

The present invention fills this need by providing highly sensitive and specific chromogenic, fluorogenic, and fluorescence polarization peptide substrates which are useful in the discovery of inhibitors of HCV proteases. The substrates of the invention are particularly useful in progress curve analysis for reversible and irreversible binding inhibitors of HCV NS3 serine protease.

The invention provides chromogenic HCV substrates comprising a chromophore covalently bonded to a peptide sequence, wherein the peptide sequence is a sequence, a subsequence, a mutated sequence or a mutated subsequence of a substrate of the HCV NS3 protease. In preferred embodiments, the peptide sequence is derived from the P side of the HCV NS3 protease cleavage site and the chromophore is covalently attached via an amide or ester bond to the carboxyl terminus of the peptide sequence.

The invention further provides fluorogenic HCV substrates comprising a fluorophore linked to a peptide sequence, wherein the peptide sequence is a sequence, a subsequence, a mutated sequence or a mutated subsequence of a substrate of the HCV NS3 protease. In preferred embodiments, the peptide sequence is derived from the P side of an HCV NS3 protease cleavage site and the fluorophore is covalently attached via an amide or ester bond to the carboxyl terminus of the peptide sequence.

The invention still further provides fluorescence polarization HCV NS3 protease substrates comprising a peptide sequence linked at opposite ends of the HCV NS3 protease cleavage site to a fluorophore and a high molecular weight ("MW") molecule binding moiety, wherein the peptide sequence is a sequence, a subsequence, a mutated sequence or a mutated subsequence of a substrate of the HCV NS3 protease. In preferred embodiments, the peptide sequence comprises both P and P' amino acid sequence from the HCV NS3 protease cleavage site, and the high MW molecule binding moiety and the fluorophore molecule are covalently attached to separate residues on the P and P' regions of the peptide via an amide bond.

The present invention also provides a method of identifying an HCV NS3 protease inhibitor and a method of assaying the catalytic efficiency of an HCV NS3 protease which utilize the novel substrates of the invention.

DETAILED DESCRIPTION OF THE NVENTION

The teachings of all references cited are incorporated herein in their entirety by reference.

The present invention includes novel chromogenic, fluorogenic, and fluorescence polarization substrates which are based upon the HCV nonstructural polyproteins which are substrates for the HCV NS3 protease. The HCV NS3 protease cleaves the polyprotein and separates the 4A/4B, 4B/5A, and 5A/5B regions of the HCV polyprotein. Using the assays described below, one can determine whether or not and to what extent the HCV NS3 protease has cleaved the substrate which is used. If a dose-dependent inhibition of substrate cleavage is observed, then the substance being tested is a potential candidate of HCV NS3 protease inhibitor.

The chromogenic and fluorogenic substrates of the present invention allow not only single end-point high throughput protease assays, but also continuous monitoring of inhibition kinetics and rapid chararterization of HCV NS3 protease inhibitors (especially irreversible or slow and/or tight binding reversible inhibitors). Due to the essential lack of P' sequences, these types of substrates, in conjunction with substrates containing both P and P' sequences, also aid in the classification of inhibitors binding to either the S or S' pocket.

The fluorescence polarization substrates of the present invention allow for highly sensitive and rapid screening of HCV NS3 protease inhibitors. In addition, assays with the disclosed fluorescence polarization substrates tolerate compounds that absorb light in the excitation and/or emission wavelength regions of the fluorophore.

The chromogenic, fluorogenic and fluorescence polarization substrates of the present invention, in particular the ester-based chromogenic and fluorogenic substrates and fluorescence polarization based substrates, provide optimized specificity, better cleavage efficiency, and improved detectability compared to prior art substrates.

As used herein, the term "HCV NS3 protease" includes any HCV derived polyprotein sequence or subsequence which exhibits HCV NS3 protease activity. The term includes, but is not limited to, the full length native NS3 protease or truncations thereof, the catalytic domain of the NS3 protease or truncations thereof, or fusion proteins of the above to an NS4A cofactor or truncation thereof. (See, for example, Urbani et al., 1997, *J. Biol Chem.* 272(14) :9204–09; Steinkuhler et al., 1996, *J. Virology* 70(10): 6694–6700; Landro et al., 1997, *Biochemistry* 36:9340–48; Zhang et al., 1997, *J. Virology* 71(8):9340–48; Failla et al., 1994, *J. Virol.* 68:3753–3760; Bartenschlager et al., 1995, *J. Virol.* 69:4377–80; Lin et al., 1995, *J. Virol.* 69:4377–80; Grakoui et al., 1993, *J. Virol* 67:2832–43; Tomei et al., 1993, *J. Virol* 67:4017–26).

CHROMOGENIC AND FLUOROGENIC SUBSTRATES

GENERAL DESIGN PRINCIPLES

The substrates of the invention can be synthesized by a suitable method such as by solid phase and/or solution phase synthesis (Merrifield, *J. Am. Chem. Soc.* 85:2149(1963)). Scheme 1 provides a schematic representation of a chromogenic or fluorogenic substrate of the present invention.

Scheme 1.
Schematic Presentation of Chromogenic or Fluorogenic Substrates of the Present Invention

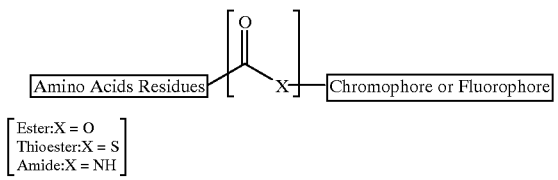

As can be seen from Scheme 1, the chromogenic and fluorogenic substrates of the present invention comprise a chromophore or a fluorophore covalently bonded to a peptide sequence, wherein the peptide sequence is a sequence, a subsequence, a mutated sequence or a mutated subsequence of a substrate of the HCV NS3 protease. In preferred embodiments, the peptide sequence is derived from the P side of the HCV NS3 protease cleavage site and the chromophore or fluorophore is covalently attached via an amide or ester bond to the carboxyl terminus of the peptide sequence.

The peptide portion of the disclosed chromogenic and fluorogenic substrates of the present invention can be of various lengths. The substrates of the present invention should be designed at an optimal length to confer substrate binding affinity and specificity. In one embodiment of the present invention, the chromogenic or fluorogenic substrates contain less than 20 amino acid residues from the P side of the HCV NS3 protease cleavage site. In more preferred embodiments, the substrates of the present invention contain 6–14 residues from the P side of the cleavage site. Most preferably, 8–12 residues from the P side of the HCV NS3 protease cleavage site are used to design the chromogenic and fluorogenic substrates.

The terms "sequence, subsequence, mutated sequence or mutated subsequence of a substrate of the HCV NS3 protease" as used herein shall have the meanings understood in the art. Specifically, the peptide portions of the substrates of the present invention may be derived from any trans cleavage site of various strains of HCV (i.e. NS4A/4B, NS4B/5A, or NS5A/5B). The term "cleavage site" as used herein refers to the HCV NS4A/4B, NS4B/5A and NS5A/5B cleavage sites as defined in Grakoui et al., 1993, *J. Virol* 67:2832–43, Tomei et al., 1993, *J. Virol* 67:4017–26, or Okamoto et al., 1994, *Intervirology* 37:68–76. In addition, certain positions in the sequence may be mutated to nonnative residues to modulate and achieve the desired water solubility, binding affinity, cleavage specificity and efficiency. For example, a Pro residue at the P2 position, while native to NS4B/5A substrate, is a good substitution for NS5A/5B derived substrates since it significantly increases the water solubility and cleavage efficiency. A nonsulfhydryl-containing residue at the P1 position can be used to moderate the catalytic efficiency of certain highly cleavable chromogenic and fluorogenic substrates. Other conservative amino acid substitutions may also be made provided they do not affect the ability of the HCV NS3 protease to cleave at the cleavage site.

The attachment of the chromophore or fluorophore to the peptide portions of the disclosed substrates is by the scissile bond. The scissile bond between the amino acid residue and the chromophore or fluorophore may be an amide, ester or thioester linkage, depending on the chromophore or fluorophore used and the need for the cleavage efficiency and stability to autohydrolysis.

An ideal chromophore or fluorophore should have a reasonably high extinction coefficient at its absorbance maximum which is well separated from the absorption spectrum of corresponding substrate conjugated with the chromophore or fluorophore (at least about 2000 OD $M^{-1}$ $cm^{-1}$). Preferred embodiments of the present invention comprise a chromophore selected from the group consisting of nitroanilines, dinitroanilines, chloronitroanilines, nitrophenols, 4-phenylazophenol, and 7-hydroxy-4-methylcoumarin. A fluorophore should also have a good fluorescence quantum yield (at least about 50%) and photostability. These factors contribute to a practical limit of detection. Preferred fluorogenic substrates of the present invention comprise a fluorophore selected from the group consisting of amino and hydroxyl derivatives of coumarin, naphthalene, quinoline, fluorene and acridine.

Nitroanilide Based Chromogenic Substrates

Preferred embodiments of the nitroanilide based chromogenic substrates of the present invention are provided below (SEQ ID NOs: 1–4):

| | |
|---|---|
| GADTEDVVKC-(4-nitroanilide) | (SEQ ID NO: 1) |
| SSGADTEDVVCC-(4-nitroanilide) | (SEQ ID NO: 2) |
| (Ac-)DTEDVVAC-(3,5-dinitroanilide) | (SEQ ID NO: 3) |
| (Ac-)GADTEDVVAC-(2-Cl-4-nitroanilide) | (SEQ ID NO: 4) |

Note: Ac = N-acetyl.

Each of the chromogenic substrates of SEQ ID NOs: 1–4 is based upon the HCV NS5A/5B cleavage site. Eight to twelve residues from the P side of the cleavage site confer substrate binding affinity and specificity.

A preferred synthetic protocol for the nitroanilide based chromogenic substrates of the present invention is provided schematically in Scheme 2, below. The chromogenic peptides of SEQ ID NOs: 1–4 were prepared by segment condensation or stepwise assembly. In the segment condensation approach, the protected peptide acid fragment was first obtained from either solution or solid phase synthesis. The anilide was then formed by coupling the protected peptide acid (diethyl ether washed) with the appropriate substituted anilines in the presence of phosphorus oxychloride $POCl_3$ in anhydrous pyridine at −15° C. for 1–2 hours (Rijkers et al, 1995, *Tetrahedron*, 51(41):11235–11250). In the stepwise assembly approach (Bernhardt et al, 1997, *Journal of Peptide Research*, 50: 143–152), Fmoc-Cys(S- trityl)-anilide was prepared similarly as mentioned above. The S-trityl group was removed by 92.5% trifluoroacetic acid ("TFA") in the presence of scavengers (2.5% water, 2.5% ethanedithiol ("EDT"), 2.5% triisopropylsilane ("TIS")). The diethyl ether washed Fmoc-Cys(SH)-anilide was anchored via the side chain thiol functional group to 2-chlorotrityl chloride resin ("2-Cl-Trt-Cl-resin") in dichloromethane ("DCM"). in the presence of diisopropylethylamine ("DIEA"). The Fmoc group is then removed and the remaining amino acid residues are sequentially assembled by solid phase peptide synthesis. Final ("TFA") cleavage afforded the correct nitroanilide substrates. The peptide substrate was purified by HPLC. The molecular mass was confirmed by electrospray ionization mass spectroscopy.

Scheme 2
A Preferred Synthetic Protocol for Nitroanilide Based Substrates of the Present Invention

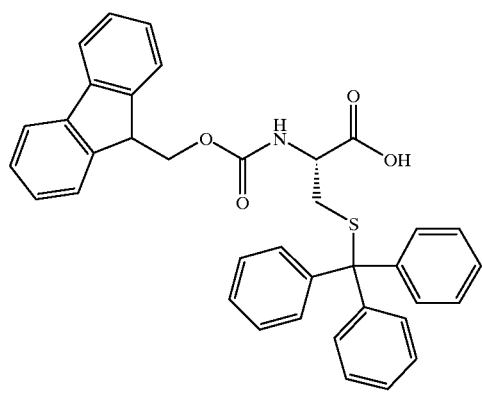

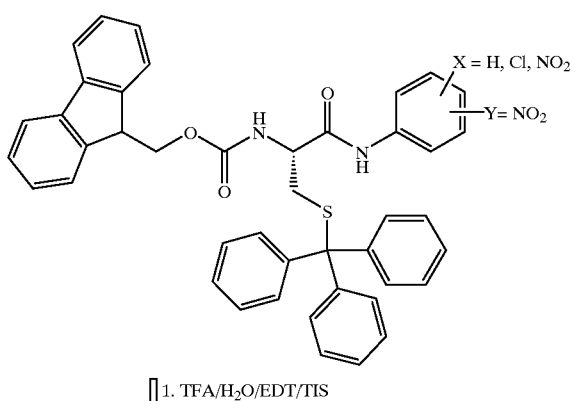

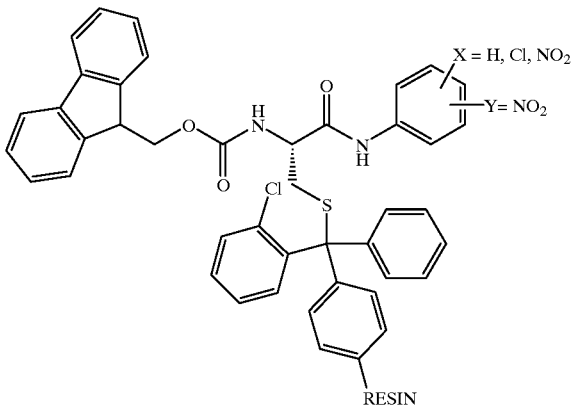

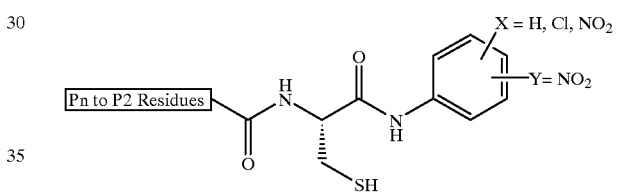

Nitrophenyl and Other Esters Based Chromogenic Substrates of the Present Invention Preferred embodiments of the nitrophenyl and other ester based chromogenic substrates of the present invention are provided below (SEQ ID NOs: 5–13):

| | |
|---|---|
| Ac-DTEDVVA(Abu)-O-4Np | (SEQ ID NO: 5) |
| Ac-DTEDVVA(Nva)-O-4Np | (SEQ ID NO: 6) |
| Ac-SSGADTEDVVA(Nva)-O-4Np | (SEQ ID NO: 7) |
| Ac-DTEDVVA(Nva)-O-3Np | (SEQ ID NO: 8) |
| GADTEDVVA(Nva)-O-3Np | (SEQ ID NO: 9) |
| Ac-DTEDVVA(Nva)-O-HMC | (SEQ ID NO: 10) |
| Ac-DTEDVVP(Nva)-O-HMC | (SEQ ID NO: 11) |
| Ac-DTEDVVA(Nva)-O-PAP | (SEQ ID NO: 12) |
| Ac-DTEDVVP(Nva)-O-PAP | (SEQ ID NO: 13) |

Key to abbreviations:
Ac=N-acetyl. Abu=L-α-aminobutyric acid residue. Nva=L-α-norvaline residue. 4 (or 3)Np=4- (or 3)-nitrophenol. HMC=7-hydroxy-4-methyl-coumarin. PAP=4-phenylazophenol.

A preferred synthetic protocol for nitrophenyl ester based substrates is provided below in Scheme 3. The chromogenic substrates of SEQ ID NOs: 5–13 were synthetically made as follows:

Fmoc-Abu (or Nva)-OH was anchored to 2-chlorotrityl chloride resin, followed by sequential peptide assembly with Fmoc chemistry. The protected peptide acid fragment was cleaved from the resin using 10% acetic acid ("HOAc"), 10% trifluoroethanol ("TFE"), 80% dichloromethane ("DCM"). The ethyl ether washed peptide fragment was dissolved in anhydrous pyridine, to which were added nitrophenol (10 molar equivalents) or other chromophores (not shown) and a catalytic amount of para-toluenesulfonic acid ("pTSA") (0.1 eq.) (adapted from Holmberg and Hansen, 1979, *Acta Chemica Scandinavica* B33: 410–412). Dicyclohexycarbodiimide (DCC) (1.5–3 eq.) was added to initiate the coupling reaction. After three days, the pyridine was evaporated in vacuo and coevaporated with toluene. The peptide substrate was deprotected with 95% trifluoroacetic acid (TFA) in dichloromethane ("DCM"). Excess chromophore was extracted by ethyl ether. The peptide substrate was purified by HPLC. The molecular mass was confirmed by electrospray ionization mass spectroscopy.

Scheme 3
A Preferred Synthetic Protocol for Nitrophenyl Ester Based Substrates

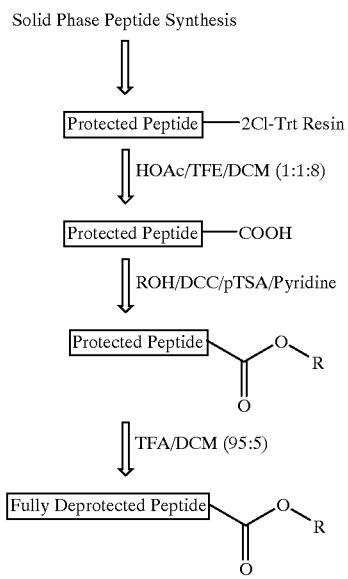

ROH = 4-(or 3-) nitrophenol, 7-hydroxy-4-methyl-coumarin, 4-phenylazophenol, etc.

Fluorogenic Substrates

Preferred embodiments of the fluorogenic substrates of the present invention are provided below (SEQ ID NOs: 14, 15, 10 & 11):

| | |
|---|---|
| Ac-DTEDVVCC-(7-amido-4-methylcoumarin) | (SEQ ID NO: 14) |
| GADTEDVVA(Nva)-(9-hydroxy-4-methoxyacridine ester) | (SEQ ID NO: 15) |
| Ac-DTEDVVA(Nva)-(7-hydroxy-4-methylcoumarin ester) | (SEQ ID NO: 10) |
| Ac-DTEDVVP(Nva)-(7-hydroxy-4-methylcoumarin ester) | (SEQ ID NO: 11) |

Peptides containing an amide linkage at the scissile bond were prepared similarly as for nitroanilides. More labile fluorogenic substrates containing ester or thioester linkage may also be synthesized similarly as for the nitrophenyl esters.

Fluorescence Polarization Substrates

Scheme 4 provides a schematic presentation of a fluorescence polarization substrate of the present invention.

Scheme 4
Schematic Presentation of a Fluorescence Polarization Substrate of the Present Invention

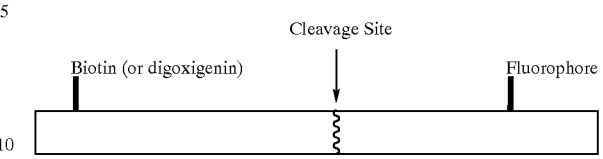

As can be seen from Scheme 4, the fluorescence polarization HCV substrates of the present invention comprise a peptide sequence linked at opposite ends of the cleavage site to a fluorophore and a high molecular weight ("MW") molecule binding moiety, wherein the peptide sequence is a sequence, a subsequence, a mutated sequence or mutated subsequence of a substrate of the HCV NS3 protease. In preferred embodiments, the peptide sequence comprises both P and P' amino acid sequence from the HCV NS3 protease cleavage site, and the high MW molecule binding moiety and the fluorophore molecule are covalently attached to separate residues on the P and P' regions of the peptide via an amide or ester bond. The fluorescence polarization substrates of the present invention contain a fluorophore and a high MW molecule binding moiety (such as biotin or digoxigenin) covalently linked to separate residues on the P and P' regions.

The term "high MW molecule binding moiety" as used herein refers to a moiety which binds a molecule which will slow down the rotation of the fluorophore on the substrate. In preferred embodiments of the present invention, the high MW molecule binding moiety is biotin or digoxigenin.

Like those of the chromogenic and fluorogenic substrates of the invention, the peptide portion of the disclosed fluorescence polarization substrates can vary in length. In preferred embodiments, the substrate contains less than 30 amino acid residues. In more preferred embodiments, 10–20 residues are used. In most preferred embodiments, the substrates of the present invention contain 12–17 amino acid residues.

Any HCV trans cleavage site can be used to design the substrate, and certain positions of the sequence may be mutated to nonnative residues to modulate and achieve the desired water solubility, binding affinity, cleavage specificity and efficiency. For example, a Pro residue at the P2 position, while native to NS4B/5A substrate, is a good substitution for NS5A/5B derived substrates since it significantly increases the water solubility and cleavage efficiency.

In preferred embodiments of the disclosed fluorescence polarization substrates of the present invention, the fluorophore is selected from the group consisting amino and hydroxyl derivatives of coumarin, naphthalene, quinoline, fluorene, and acridine, and the high molecular weight binding moiety is biotin or digoxigenin.

The substrate should be designed so that neither the fluorophore nor the high MW molecule binding moiety will interfere with the protease recognition site. Binding of a high MW molecule (such as egg white avidin, streptavidin or anti-biotin antibody (if the high MW molecule binding moiety is biotin), or anti-digoxigenin antibody (if the high MW molecule binding moiety is digoxigenin) to the high MW molecule binding moiety on the uncleaved substrate slows down the rotation of the fluorophore on the substrate and increases the fluorescence polarization. Substrate cleavage by the protease uncouples the biotin- or digoxigenin-containing product sequence and the fluorophore-containing product sequence where fluorescence polarization is not affected by high MW molecules. Thus, the overall fluorescence polarization in the presence of excess amount of high MW binding proteins will decrease with substrate cleavage.

The high MW molecule-binding moiety may be located in a manner that binding of the high MW molecule renders the protease inaccessible to the complexed substrate, effectively quenching the protease activity as required in single end-point screening assay. Alternatively, the high MW molecule-binding moiety may be placed away from the substrate binding site of the protease to allow continuous monitoring of fluorescence polarization (SEQ ID NO: 24). The fluorophore should not be so flexibly linked to the substrate as to suffer from significant "propeller effect" and lead to less pronounced fluorescence polarization (see Jolley, 1996, *J. Biomolecular Screening* 1(1):33,35). In general, a practical assay requires a difference of fluorescence polarization by at least about 0.1 to 0.2 between the free and large MW molecule bound forms of uncleaved substrates.

Preferred embodiments of the fluorescence polarization substrates of the present invention are provided below (SEQ ID NOs: 16–24):

| | |
|---|---|
| DTEDVVC(S-Fam)CSMSYK(ε-Btn) | (SEQ ID NO: 16) |
| Btn-DTEDVVCCSMSYK(ε-Ftc)K-OH | (SEQ ID NO: 17) |
| Btn-DTEDVVCCSM[DbU](γ-BODIPY FL)YR-OH | (SEQ ID NO: 18) |
| Btn-DTEDVVCCSM[DbU](γ-BODIPY TR-X)YR-OH | (SEQ ID NO: 19) |
| Btn-DTEDVVCCSMSYTWTGK(ε-BODIPY FL)-OH | (SEQ ID NO: 20) |
| Btn-DTEDVVCCSMSYTWTGK(ε-Fam)-OH | (SEQ ID NO: 21) |
| Btn-EDVVA(Abu) Ψ[COO] AMSYTWK(ε-Fam)-OH | (SEQ ID NO: 22) |
| Btn-EDVVA(Abu) Ψ[COO] AMSYTWK(ε-BODIPY FL)-OH | (SEQ ID NO: 23) |
| Btn-SSGADTEDVVA(Abu) Ψ[COO] AMSYK(ε-Fam)-OH | (SEQ ID NO: 24) |

Key to abbreviations:
Fam = fluorescein-5 (or 6)-carboxamidoyl.
Btn = biotinyl.
Ftc = fluorescen-5-thiolcarbamoyl.
Dbu = 2,3-diaminobutanoyl.
BODIPY FL = 4,4,-difluro-5,7-dimethyl-4-boro-3a,4a-diaza-s-indacene-3-propionyl.
BODIPY TR-X = 6-(((4-(4,4-difluro-5-(2-thienyl)-4-boro-3a,4a-diaza-s-indacene-3-yl)phenoxy) acetyl)amino)hexanoyl.
Ψ[COO] = ester bond in place of amide bond.

Key to abbreviations:
Fam=fluorescein-5 (or 6)-carboxamidoyl.
Btn=biotinyl. Ftc=fluorescen-5-thiolcarbamoyi. Dbu=2,3-diaminobutanoyi.
BODIPY FL=4,4,-difluro-5,7-dimethyl4-boro-3a,4a-diaza-s-indacene-3-propionyl.
BODIPY TR-X=6-(((4-(4,4-difluro-5-(2-thienyl)-4-boro-3a,4a-diaza-s-indacene-3-yl) phenoxy) acetyl)amino) hexanoyl.
Ψ[COO]=ester bond in place of amide bond.
BODIPY® is a registered U.S. trademark of Molecular Probes Inc., a corporation located in Eugene, Oregon. BODIPY® is a fluorescent dye used as a fluorescent label and is sold either singly or conjugated to various molecules as described in detail in the legend above.

The fluorescence polarization peptides of SEQ ID NOs: 16–24 were assembled with Fmoc chemistry. The side chain label was added selectively either during solid phase synthesis or in solution after cleavage. The backbone ester linkage between the P1 and P1' residue was introduced during the solid phase assembly by esterification of hydroxyl of (+) lactic acid at P1' position [Bianchi et al., 1996, *Analytical Biochemistry* 237:239–244].

All of the substrates of the present invention can be synthesized by suitable methods such as by exclusive solid phase synthesis, partial solid phase methods, fragment condensation or classical solution synthesis. The polypeptides are preferably prepared by solid phase peptide synthesis as described by Merrifield, *J. Am. Chem. Soc.* 85: 2149 (1963). The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g. , biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexyloxycarbonyl] and alkyl type protecting groups (e.g., benzyl, triphenylmethyl). The preferred protecting groups are tBoc and Fmoc, thus the peptides are said to be synthesized by tBoc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide. In tBoc chemistry, the side-chain protecting groups for trifunctional amino acids are mostly benzyl based. in Fmoc chemistry, they are mostly tert.-butyl or trityl based.

In tBoc chemistry, the preferred side-chain protecting groups are tosyl for Arg, cyclohexyl for Asp, 4-methylbenzyl (and acetamidomethyl) for Cys, benzyl for Glu, Ser and Thr, benzyloxymethyl (and dinitrophenyl) for His, 2-Cl-benzyloxycarbonyl for Lys, formyl and cyclohexyloxycarbonyl for Trp and 2-bromobenzyl for Tyr. In Fmoc chemistry, the preferred side-chain protecting groups are, 2,2,5,7,8pentamethylchroman-6-sulfonyl (Pmc) or 2,2,4,6,7-pentamethyldihydrobenzofuran-5-sulfonyl (Pbf) for Arg, trityl for Asn, Cys, Gln and His, tert-butyl for Asp, Glu, Ser, Thr and Tyr, tBoc for Lys and Trp.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortorityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) is used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al (1984)., "*Solid Phase Peptide Synthesis*" (2nd Edition), Pierce Chemical Co., Rockford, Ill.; and Bayer & Rapp (1986) *Chem. Pept.*

*Prot.* 3, 3; and Atherton, et al. (1989) *Solid Phase Peptide Synthesis: A Practical Approach*, IRL Press, Oxford.

The C-terminal amino acid, protected at the side-chain if necessary and at the alpha-amino group, is attached to a hydroxylmethyl resin using various activating agents including dicyclohexylcarbodiimide ("DCC"), N,N'-diisopropylcarbodiimide ("DIPCDI") and carbonyldiimidazole ("CDI"). It can be attached to chloromethyl or chlorotrityl resin directly in its cesium tetramethylammonium salt form or in the presence of triethylamine ("TEA") or diisopropylethylamine ("DIEA"). The first amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), propane phosphonic acid anhydride (PPA), benzotriazol-1-yl-oxy-tris-(dimethylamino)-phosphonium hexafluorophosphate (BOP) and its pyrrolidine analog, benzotriazol-1-yl-oxy-tris-(pyrrolidino)-phosphonium hexafluorophosphate (PyBOP), bromo-tris-pyrrolidino-phosphonium hexafluorophosphate (PyBroP), N-[(1H-benzotriazol-1-yl)(dimethylamine) methylene-]-N-methylmethanaminium hexafluorophosphate N-oxide (HBTU), 7-enzotriazol-1-yl)-1,1,3,3-tetramethyluronium tetrafluoroborate (TBTU), (N-[(dimethylamino)-1H-1,2,3-triazolo[4,5-b]pyridin-1-ylmethylene]-N-methylmethanaminium hexafluorophosphate N-oxide (HATU), 7-azobenzotriazol-1-yl-1,1,3,3-tetramethyluronium tetrafluoroborate (TATU), 1-(1-pyrrolidinyl-1H-1,2,3-triazolo[4,5-b]pyridin-1-ylmethylene) pyrrolidinium hexafluorophosphate N-oxide (HAPyU), 7-azabenzotriazol-1-yl-oxytris(pyrrolidino) phosphonium hexafluorophosphate (PyAOP), and tetramethyl fluoroformamidinium hexafluorophosphate (TFFH). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction can be monitored at each stage, e.g., by the ninhydrin reaction as described by Kaiser et al., *Anal. Biochem.* 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired peptide, the peptide-resin is cleaved with a reagent with proper scavengers. The Fmoc peptides are usually cleaved and deprotected by TFA with scavengers (e.g., $H_2O$, ethanedithiol, triisopropylsilane, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of Trp and dinitrophenyl group of His need to be removed, respectively, by piperidine and thiophenol in DMF prior to the HF cleavage. The acetamidomethyl group of Cys can be removed by mercury(II) acetate and alternatively by iodine, thallium (III) trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

Recombinant DNA methodology can also be used to prepare the peptide portion of the substrates. The known genetic code, tailored if desired with known preferred codons for more efficient expression in a given host organism, can be used to synthesize oligonucleotides encoding the desired amino acid sequences. The phosphoramidite solid support method of Matteucci et al., *J. Am. Chem. Soc.* 103:3185 (1981) or other known methods can be used for such syntheses. The resulting oligonucleotides can be inserted into an appropriate vector and expressed in a compatible host organism.

The peptides of the invention can be purified using HPLC, gel filtration, ion exchange and partition chromatography, countercurrent distribution or other well known methods.

DNA encoding the peptide portions of the substrates of this invention can be prepared by chemical synthesis using the known nucleic acid sequence [Ratner et al., Nucleic Acids Res. 13:5007 (1985)] and standard methods such as the phosphoramidite solid support method of Matteucci et al. [J Am. Chem. Soc. 103:3185 (1981)] or the method of Yoo et al. [J. Biol. Chem. 764:17078 (1989)]. See also Glick, Bernard R. and Pasternak, *Molecular Biotechnology: pages 55–63*, (ASM Press, Washington, D.C. 1994). The gene encoding the desired cleavage site can also be obtained using the plasmid disclosed in Grakoui, A., Wychowski, C., Lin, C., Feinstone, S. M., and Rice, C. M., Expression and Identification of Hepatitis C Virus polyprotein Cleavage Products, *J. Virol* 67;1385–1395 (1993). Also, the nucleic acid encoding the desired portion of the HCV polyprotein can be isolated, amplified and cloned (from patients infected with the HCV virus). Furthermore, the HCV genome has been disclosed in PCT WO 89/04669 and are available from the American Type Culture Collection (ATCC), 12301 Parklawn Drive, Rockville, Md. under ATCC accession no. 40394.

Of course, because of the degeneracy of the genetic code, there are many functionally equivalent nucleic acid sequences that can encode the HCV NS3 trans cleavage sites described herein. Such functionally equivalent sequences, which can readily be prepared using known methods such as chemical synthesis, PCR employing modified primers and site-directed mutagenesis, are within the scope of this invention.

Various expression vectors can be used to express DNA encoding the HCV NS3 cleavage sites. Conventional vectors used for expression of recombinant proteins in prokaryotic or eukaryotic cells may be used. Preferred vectors include the pcD vectors described by Okayama et al., *Mol. Cell. Bio. Vol.* 3: 280–289 (1983); and Takebe et al., *Mol. Cell. Biol. Vol.* 8: 466–472 (1988). Other SV40-based mammalian expression vectors include those disclosed in Kaufman et al., *Mol. Cell. Biol. Vol.* 2:1304–1319 (1982) and U.S. Pat. No. 4,675,285. These SV40-based vectors are particularly useful in COS7 monkey cells (ATCC No. CRL 1651), as well as in other mammalian cells such as mouse L cells and CHO cells.

Standard transfection methods can be used to produce eukaryotic cell lines which express large quantities of the polypeptide. Eukaryotic cell lines include mammalian, yeast and insect cell lines. Exemplary mammalian cell lines include COS7 cells, mouse L cells and Chinese Hamster Ovary (CHO) cells. See Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology*, Greene and Wiley, N.Y.

As used herein, the term "transformed bacteria" means bacteria that have been genetically engineered to produce a mammalian protein. Such genetic engineering usually entails the introduction of an expression vector into a bacterium. The expression vector is capable of autonomous replication and protein expression relative to genes in the bacterial genome. Construction of bacterial expression is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.*83:599 (1986), Sproat et al., *Nucleic Acid Research* 13:2959 (1985) and Mullenbach et al., *J. Biol. Chem* 261:719 (1986) disclose how to construct synthetic genes for expression in bacteria. Many bacterial expression vectors are available commercially and through the American Type Culture Collection (ATCC), Rockville, Md.

Insertion of DNA encoding human HCV protease into a vector is easily accomplished when the termini of both the DNA and the vector comprise the same restriction site. If this is not the case, it may be necessary to modify the termini of the DNA and/or vector by digesting back single-stranded DNA overhangs generated by restriction endonuclease cleavage to produce blunt ends, or to achieve the same result by filling in the sing -stranded termini with an appropriate DNA polymerase. Alternatively, any site desired may be produced by ligating nucleotide sequences (linkers) onto the termini. Such linkers may comprise specific oligonucleotide sequences that define desired restriction sites. The cleaved vector and the DNA fragments may also be modified if required by homopolymeric tailing.

Many *E. coli*-compatible expression vectors can be used to produce HCV peptides, including but not limited to vectors containing bacterial or bacteriophage promoters such as the Tac, Lac, Trp, LacUV5, 1 $P_r$ and 1 $P_L$ promoters. Preferably, a vector selected will have expression control sequences that permit regulation of the rate of HCV protease expression. Then, HCV peptide production can be regulated to avoid overproduction that could prove toxic to the host cells. Most preferred is a vector comprising, from 5' to 3' (upstream to downstream), a Tac promoter, a lac Iq repressor gene and DNA encoding mature human HCV protease. The vectors chosen for use in this invention may also encode secretory leaders such as the ompA or protein A leader, as long as such leaders are cleaved during post-translational processing to produce mature HCV protease or if the leaders are not cleaved, the leaders do not interfere with the enzymatic activity of the protease.

Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) Current Protocols in Molecular Biology, Greene and Wiley, N.Y. Techniques for synthesis of polypeptides are described, e.g., in Merrifield (1963) *J. Amer. Chem. Soc.* 85:2149–2156; Merrifield (1986) *Science* 232: 341–347; and Stewart et al (1984)., "Solid Phase Peptide Synthesis" (2nd Edition), Pierce Chemical Co., Rockford, IL.; and Atherton, et al. (1989) Solid Phase Peptide Synthesis: A Practical Approach, IRL Press, Oxford; and Grant (1992) Synthetic Peptides: A User's Guide, W. H. Freeman, N.Y.

The chromophore or fluorophore can then be attached to the recombinantly produced peptide portion of the substrate by HCV NS3 protease-catalyzed synthesis in organic solvent (or low-water activity solvent). Alternatively, a semi-synthetic approach may be used where an aminoacyl (or peptidyl) chromophore (or fluorophore) is coupled to a recombinant peptide fragment by "reverse hydrolysis" of a non-HCV protease which specifically recognizes the carboxyl terminal residue of the recombinant peptide and/or the amino terminal residue on the amino acyl (or peptidyl) chromophore (or fluorophore).

A fluorescence polarization peptide substrate containing two molecular tags may also be prepared from the recombinantly produced peptide. The cysteine sulffydryl group, if present, may be oxidized to disulfide first before site-specific labelings of proper molecular tags, a fluorophore and the high MW molecule binding moiety (biotin or digoxigenin). The first tag, in its properly activated form (e.g., N-hydroxysuccinimide ester), may be then selectively attached to the amino terminus of the peptide in an aqueous solution near neutral pH. Finally, a lysine sidechain amino group can be selectively modified at neutral to alkaline pH (7 to 9) by a second activated tag. Alternatively, the second tag may be first attached to a lysine sidechain or carboxyl terminus of a small peptide which then is coupled to the recombinant peptide containing the first tag at amino terminus, using reverse hydrolysis as described above.

One can use the novel substrates of this invention to develop high throughput assays. These can be used to assay cleavage efficiency or to screen for compounds which inhibit proteolytic activity of the protease.

The following examples are included to illustrate, but not to limit, the present invention.

EXAMPLE 1

Nitroanilide Based Chromogenic Substrates

The chromogenic substrates defined by SEQ ID NOs: 1–4 were synthetically produced as described above and tested for cleavage efficiency in 25 mM MOPS buffer, pH 7.5, containing 10% (v/v) glycerol, 0.15 M NaCl, 0.2% lauryl maltoside and 10 mM DTT. The HCV NS3 protease used in our assays was a non-covalent complex of full-length HCV 1a(H) (SEQ ID NO:25) with amino acids 1–54 of the NS4A cofactor (SEQ ID NO:26) ("NS3(1–631)/4A(1–54)"). The complex was expressed in a baculovirus system as described in Sali et al, 1998, Biochemistry 37:3392–3401. The protease construct, containing an N-terminal histidine tag, was spontaneously generated by an intramolecular cleavage and purified to greater than 95% homogeneity by nickel-nitrilotriacetic acid affinity chromotography. The histidine tag was then cleaved by thrombin to yield the NS3/4A protease which was a noncovalent complex between NS4A (54 residues) and NS3 (631 residues) with an additional seven heterologous residues (GRRSTSM) at the N-terminus of NS3.

Each of the substrates was cleaved by HCV NS3(1–631)/4A(1–54). The rate of aniline product formation was monitored by a spectrophotometer at 410 run.

The results are provided in Table 1, below:

TABLE 1

Catalytic Efficiency of Nitroanilide Based Substrates

| Nitroanilide Substrate | kcat (min-1) | Km ($\mu$M) | kcat/Km (M-1s-1) |
|---|---|---|---|
| GADTEDVVKC-(4-nitroanilide) (SEQ ID NO: 1) | 0.2 | 200 | 15 |
| SSGADTEDVVCC-(4-nitroanilide) (SEQ ID NO: 2) | 0.2 | 75 | 45 |
| (Ac-)GADTEDVVAC-(2-Cl-4-nitroanilide) (SEQ ID NO: 4) | ND | ND | 10 |

ND = Not Determined

EXAMPLE 2

Nitrophenyl and Other Ester Based Chromogenic Substrates

The chromogenic substrates defined by SEQ ID NOs: 5–13 were synthetically produced as described above and tested for cleavage efficiency in 25 mM MOPS buffer, pH 6.5, containing 10% (v/v) glycerol, 0.15 M NaCl, 0.2% lauryl maltoside. The substrates were cleaved by NS3/4A (1–631)/4A(1–54) (see Example 1). The rate of product formation was monitored by a spectrophotometer, at 400 nm for 4Np, 370 nm for PAP, and 340 nm for 3Np and HMC.

TABLE 2

Catalytic Efficiency of Nitrophenyl and Other Esters Based Substrates

| Ester Substrate | kcat (min-1) | Km ($\mu$M) | kcat/Km (M-1s-1) |
|---|---|---|---|
| Ac-DTEDVVA(Nva)-O-4Np (SEQ ID NO: 6) | 36 | 16 | 38,000 |
| Ac-SSGADTEDVVA(Nva)-O-4Np (SEQ ID NO: 7) | 14 | 9 | 25,000 |
| Ac-DTEDVVP(Nva)-O-PAP (SEQ ID NO: 13) | 14 | 18 | 13,000 |
| GADTEDVVA(Nva)-O-3Np (SEQ ID NO: 9) | 20 | 30 | 11,100 |
| Ac-DTEDVVA(Nva)-O-HMC (SEQ ID NO: 16) | 10 | 20 | 8,400 |
| Ac-DTEDVVP(Nva)-O-HMC (SEQ ID NO: 11) | 20 | 40 | 8,400 |
| Ac-DTEDVVA(Nva)-O-3Np (SEQ ID NO: 8) | 21 | 48 | 7,300 |
| Ac-DTEDVVA(Nva)-O-PAP (SEQ ID NO: 12) | 4 | 17 | 4,000 |

As can be seen from Table 2, all ester based substrates were very well cleaved. The autohydrolysis rate measured at pH 6.5 was negligible for 4-phenylazophenyl ester substrates (<0.08% per min), minimal for 7-hydroxy-4-methylcoumarinyl ester and 3-nitrophenyl ester peptide substrates (<0.15% per min), but more pronounced for 4-nitrophenyl ester peptide substrates.

EXAMPLE 3

Fluorogenic Substrates

The fluorogenic substrates of the invention are synthetically produced as described above in Scheme 2, and dissolved in an assay buffer prepared from ultralow fluorescence grade reagent, containing 25 mM MOPS buffer, pH 7.5, containing 10% (v/v) glycerol, 0.15 M NaCl, 0.2% lauryl maltoside. To test for cleavage efficiency, the substrate cleavage by HCV NS3 is monitored continuously by a spectrofluorometer. The excitation and emission wavelengths used to detect the release of the fluorophore depend on the specific fluorophore used and the extent of spectral overlap between the substrate and the free fluorophore. Generally, off-peak detection is used to minimize the interference from the substrate. For example, the methylcoumarin-containing substrates cleavage may be detected at ~460 nm with excitation at ~380 nm, acridine-containing substrate may be detected at much higher wavelengths (e.g., emission at ~460 nm and excitation at ~580 nm).

The cleavage efficiency for the ester substrates derived from 7-hydroxy-4-methylcoumarin (SEQ ID NOs: 10 and 11) in an assay using NS3/4A(1–163)/4A(1–54) (see Example 1) are reported in Table 2. All fluorogenic substrates have the dual advantage of being detected at either the absorption or emission wavelength, although detection at the emission wavelength by a spectrofluorometer generally provides much more sensitivity.

EXAMPLE 4

Florescence Polarization Substrates

The fluorescence polarization substrates defined by SEQ ID NOs 16–24 were synthetically produced using Fmoc chemistry as described in Scheme 2 and tested for cleavage efficiency in 25 mM Tris buffer, pH 7.5, containing 10% (v/v) glycerol, 0.15 M NaCl, 0.05% lauryl maltoside. The substrates were cleaved by HCV NS3/4A (SEQ ID NO: 25) which was recombinantly expressed in and purified from insect cells (Sali et al, 1998, *Biochemistry*, 37: 3392–3401). HPLC was used to quantitate the product formation.

Most of the fluorescence polarization substrates were readily cleaved, with catalytic efficiency up to 30,000 M$^{-1}$ s$^{-1}$ for biotinylated amide substrates and 460,000 M$^{-1}$ s$^{-1}$ for biotinylated ester substrate. The maximal difference of fluorescence polarization between free and avidin bound forms of uncleaved substrates were 0.1 to 0.22, as determined with FMP-1 (olley Consulting and Research, Inc., Grayslake, Ill.). This difference of polarization was sufficient for analysis of inhibition kinetics. The 96-well plate reader of FMP-2 was also evaluated and found to reproduce the necessary polarization difference. Substrates of SEQ ID NOs:16–23 may be used for single end-point assay. The substrate of SEQ ID NO:24 may be used for continuous monitoring assay.

EXAMPLE 5

HCV NS3 Protease Assays using Chromogenic Substrates

To test the proteolytic activity of an HCV NS3 protease, place a chromogenic substrate of the present invention and a soluble HCV NS3 protease together in an assay buffer (25 mM MOPS buffer, pH 6.5, containing 10% (v/v) glycerol, 0.15 M NaCl, 0.2% lauryl maltoside) in a 96-well plate. Detect the cleavage of the chromophore off the substrate by the protease in a continuous mode at 370 run with a SpectraMax Plus 96-well plate reader (Molecular Devices, Sunnyvale, Calif.). Perform proper controls for autohydrolysis and generate a standard curve for the chromophore simultaneously.

EXAMPLE 6

HCV NS3 /4A Protease Assays Using Fluorogenic Substrates

To test the proteolytic activity of an HCV NS3 protease, a fluorogenic substrate of the present invention and a soluble HCV NS3 protease are placed together in an assay buffer prepared from ultralow fluorescence grade reagent, containing 25 mM MOPS buffer, pH 7.5, containing 10% (v/v) glycerol, 0.15 M NaCl, 0.2% lauryl maltoside. The substrate cleavage by HCV NS3/4A is monitored continuously by a spectrofluorometer. The excitation and emission wavelengths used to detect the release of the fluorophore depend on the specific fluorophore used and the extent of spectral overlap between the substrate and the free fluorophore. Generally, off-peak detection is used to minimize the interference from the substrate. For example, cleavage of the methylcoumarin-containing substrates may be detected at ~460 nm with excitation at ~380 nm, acridine-containing substrate may be detected at much higher wavelengths (e.g., emission at ~460 run and excitation at ~580 nm).

EXAMPLE 7

HCV NS3/4A Protease Assays Using Fluorescence Polarization Substrates

Any fluorescence polarization substrate of the present invention can be used in an assay to test the proteolytic activity of an HCV NS3 protease using the protocol set forth in Example 4.

We claim:

1. A chromogenic HCV substrate comprising a single chromophore selected from the group consisting of nitrophenols, 4-phenylazophenol, and 7-hydroxy4-methylcoumarin linked to the C-terminus of a peptide sequence, wherein the peptide sequence is a sequence, a subsequence, a mutated sequence or a mutated subsequence of a substrate of the HCV NS3 protease.

2. The chromogenic HCV substrate of claim 1, wherein the peptide sequence is less than 20 amino acid residues.

3. The chromogenic HCV substrate of claim 2, wherein the peptide sequence is 6–14 amino acid residues.

4. The chromogenic HCV substrate of claim 3, wherein the peptide sequence is 8–12 amino acid residues.

5. The chromogenic HCV substrate of claim 1, wherein the peptide sequence is derived from the NS4A/4B cleavage site of the HCV polyprotein sequence.

6. The chromogenic HCV substrate of claim 1, wherein the peptide sequence is derived from the NS4B/5A cleavage site of the HCV polyprotein sequence.

7. The chromogenic HCV substrate of claim 1, wherein the peptide sequence is derived from the NS5A/5B cleavage site of the HCV polyprotein sequence.

8. The chromogenic HCV substrate of claim 1, having the structure defined by SEQ ID NOs: 1–13.

9. A method for assaying the catalytic efficiency of an HCV NS3 protease, comprising (a) contacting an HCV NS3 protease with a peptide substrate of claim 1 under conditions in which proteolysis can occur; and (b) detecting whether and to what extent HCV NS3 protease has cleaved the substrate.

10. A method for identifying an HCV NS3 protease inhibitor, comprising (a) contacting an HCV NS3 protease with a peptide substrate of claim 1 and a suspected protease inhibitor under conditions in which proteolysis can occur; and (b) detecting whether and to what extent the HCV NS3 protease has cleaved the substrate.

11. A fluorogenic HCV substrate comprising a single fluorophore linked to the C-terminus of a peptide sequence, wherein the peptide sequence is a sequence, a subsequence, a mutated sequence or mutated subsequence of a substrate of the HCV NS3 protease, and the peptide sequence is derived from the NS4A/4B, NS4B/5A, or NS5A/5B cleavage site of the HCV polyprotein sequence.

12. The fluorogenic HCV substrate of claim 11, wherein the peptide sequence is less than 20 amino acid residues.

13. The fluorogenic HCV substrate of claim 12, wherein the peptide sequence is 6–14 amino acid residues.

14. The fluorogenic HCV substrate of claim 13, wherein the peptide sequence is 8–12 amino acid residues.

15. The fluorogenic HCV substrate of claim 11, wherein the peptide sequence is derived from the NS4A/4B cleavage site of the HCV polyprotein sequence.

16. The fluorogenic HCV substrate of claim 11, wherein the peptide sequence is derived from the NS4B/5A cleavage site of the HCV polyprotein sequence.

17. The fluorogenic HCV substrate of claim 11, wherein the peptide sequence is derived from the NS5A/5B cleavage site of the HCV polyprotein sequence.

18. The fluorogenic HCV substrate of claim 11, wherein the fluorophore is selected from the group consisting of amino and hydroxyl derivatives of coumarin, naphthalene, quinoline, fluorene, and acridine.

19. The fluorogenic HCV substrate of claim 11, having the structure defined by SEQ ID NO: 10, 11, 14 or 15.

20. A method for assaying the catalytic efficiency of an HCV NS3 protease, comprising (a) contacting an HCV NS3 protease with a peptide substrate of claim 11 under conditions in which proteolysis can occur; and (b) detecting whether and to what extent the HCV NS3 protease has cleaved the substrate.

21. A method for identifying an HCV NS3 protease inhibitor comprising (a) contacting an HCV NS3 protease with a peptide substrate of claim 11 and a suspected protease inhibitor under conditions in which proteolysis can occur; and (b) detecting whether and to what extent the HCV NS3 protease has cleaved the substrate.

22. A fluorescence polarization HCV substrate comprising a peptide sequence linked at opposite ends of the cleavage site to a fluorophore and a high molecular weight (MW) binding moiety, wherein the peptide sequence is a sequence, a subsequence, a mutated sequence or mutated subsequence of a substrate of the HCV NS3 protease, and wherein the fluorophore is selected from the group consisting of amino and hydroxyl derivatives of coumarin, naphthalene, quinoline, fluorene, and acridine.

23. The fluorescence polarization substrate of claim 22, wherein the peptide sequence has less than 30 amino acid residues.

24. The fluorescence polarization substrate of claim 22, wherein the peptide sequence has 10–20 amino acid residues.

25. The fluorescence polarization substrate of claim 22, wherein the peptide sequence has 12–17 amino acid residues.

26. The fluorescence polarization substrate of claim 22, wherein the peptide sequence is derived from the NS4A/4B cleavage site of the HCV polyprotein sequence.

27. The fluorescence polarization substrate of claim 22, wherein the peptide sequence is derived from the NS4B/5A cleavage site of the HCV polyprotein sequence.

28. The fluorescence polarization substrate of claim 22, wherein the peptide sequence is derived from the NS5A/5B cleavage site of the HCV polyprotein sequence.

29. The fluorescence polarization substrate of claim 22, wherein the high molecular weight binding moiety is selected from the group consisting of biotin and digoxigenin.

30. The fluorescence polarization substrate of claim 22, having the structure defined by SEQ ID NO: 16, 17, 18, 19, 20, 21, 22, 23 or 24.

31. A method for assaying the catalytic efficiency of an HCV NS3 protease comprising (a) contacting an HCV NS3 protease with a peptide substrate of claim 22 under conditions in which proteolysis can occur; and (b) detecting whether and to what extent the HCV NS3 protease has cleaved the substrate.

32. A method for identifying an HCV NS3 protease inhibitor, comprising (a) contacting an HCV NS3 protease with a peptide substrate of claim 22 and a suspected protease inhibitor under conditions in which proteolysis can occur; and (b) detecting whether and to what extent the HCV NS3 protease has cleaved the substrate.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (ix) FEATURE:
      (D) OTHER INFORMATION: /note= The cysteine residue at position
         10 is modified as 4-nitroanilide (xi) SEQUENCE DESCRIPTION: SEQ ID NO:1:

Gly Ala Asp Thr Glu Asp Val Val Lys Cys
1               5                   10

(2) INFORMATION FOR SEQ ID NO:2:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (ix) FEATURE:
      (D) OTHER INFORMATION: /note= The cysteine residue at position
         12 is modified as 4-nitroanilide (xi) SEQUENCE DESCRIPTION: SEQ ID NO:2:

Ser Ser Gly Ala Asp Thr Glu Asp Val Val Cys Cys
1               5                   10

(2) INFORMATION FOR SEQ ID NO:3:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (D) OTHER INFORMATION: /note= The aspartic acid residue at
         position 1 is N-acetylated. The cysteine residue at
         position 8 is modified as 3,5-dinitroanilide.

(xi) SEQUENCE DESCRIPTION: SEQ ID NO:3:

Asp Thr Glu Asp Val Val Ala Cys
1               5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= The glycine residue at position
            1 is N-acetylated. The cysteine residue at position 10 is
            modified as 2-Cl-4-nitroanilide.

(xi) SEQUENCE DESCRIPTION: SEQ ID NO:4:

Gly Ala Asp Thr Glu Asp Val Val Ala Cys
1               5                   10

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 8 is Abu (a-
            aminobutyric acid). The aspartic acid residue at position
            1 is N-acetylated. The Abu residue at position 8 is
            esterified with 4-nitrophenol.

(xi) SEQUENCE DESCRIPTION: SEQ ID NO:5:

Asp Thr Glu Asp Val Val Ala Xaa
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 8 is Nva
            (norvaline). The aspartic acid residue at position 1 is N-
            acetylated. The Nva at position 8 is esterified with 4-
            nitrophenol.

(xi) SEQUENCE DESCRIPTION: SEQ ID NO:6:

Asp Thr Glu Asp Val Val Ala Xaa
1               5

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear -continued (ii) MOLECULE TYPE: peptide (ix) FEATURE:
            (D) OTHER INFORMATION: /note= Xaa at position 12 is Nva
                (norvaline). The serine residue at position 1 is N-
                acetylated. The Nva residue at position 12 is esterified
                with 4-nitrophenol.

(xi) SEQUENCE DESCRIPTION: SEQ ID NO:7:

Ser Ser Gly Ala Asp Thr Glu Asp Val Val Ala Xaa
1               5                   10

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= Xaa at position 8 is Nva
                (norvaline). The aspartic acid residue at position 1 is
                N-acetylated. The Nva at position 8 is esterified with 3-
                nitrophenol.

(xi) SEQUENCE DESCRIPTION: SEQ ID NO:8:

Asp Thr Glu Asp Val Val Ala Xaa
1               5

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= Xaa at position 10 is Nva
                (norvaline). The Nva residue at position 10 is esterified
                with 3-nitrophenol.

(xi) SEQUENCE DESCRIPTION: SEQ ID NO:9:

Gly Ala Asp Thr Glu Asp Val Val Ala Xaa
1               5                   10

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= Xaa at position 8 is Nva
                (norvaline). The aspartic acid residue at position 1 is
                N-acetylated. The Nva residue at position 8 is esterified
                with 7-hydroxy-4-methyl-coumarin.

(xi) SEQUENCE DESCRIPTION: SEQ ID NO:10:

Asp Thr Glu Asp Val Val Ala Xaa
1               5

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 8 is Nva
            (norvaline). The aspartic acid residue at position 1 is
            N-acetylated. The Nva residue at position 8 is esterified
            with 7-hydroxy-4-methyl-coumarin.

(xi) SEQUENCE DESCRIPTION: SEQ ID NO:11:

Asp Thr Glu Asp Val Val Pro Xaa
1             5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 8 is Nva
            (norvaline). The aspartic acid residue at position 1 is
            N-acetylated. The Nva residue at position 8 is esterified
            with 4-phenylazophenol.

(xi) SEQUENCE DESCRIPTION: SEQ ID NO:12:

Asp Thr Glu Asp Val Val Ala Xaa
1             5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 8 is Nva
            (norvaline). The aspartic acid residue at position 1 is
            N-acetylated. The Nva residue at position 8 is esterified
            with 4-phenylazophenol.

(xi) SEQUENCE DESCRIPTION: SEQ ID NO:13:

Asp Thr Glu Asp Val Val Pro Xaa
1             5

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= The aspartic acid residue at
            position 1 is N-acetylated. The cysteine residue at postion 8 is modified as 7-amido-4-methylcoumarin.

(xi) SEQUENCE DESCRIPTION: SEQ ID NO:14:

Asp Thr Glu Asp Val Val Cys Cys
1               5

(2) INFORMATION FOR SEQ ID NO:15:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (ix) FEATURE:
       (D) OTHER INFORMATION: /note= Xaa at position 10 is Nva
           (norvaline). The Nva residue at position 10 is esterified
           with 9-hydroxy-4-methoxyacridine.

(xi) SEQUENCE DESCRIPTION: SEQ ID NO:15:

Gly Ala Asp Thr Glu Asp Val Val Ala Xaa
1               5                   10

(2) INFORMATION FOR SEQ ID NO:16:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (ix) FEATURE:
       (D) OTHER INFORMATION: /note= The cysteine residue at position
           7 is modified by fluorescein-5 (or 6)-carboxamidoyl. The
           lysine residue at position 13 is biotinylated.

(xi) SEQUENCE DESCRIPTION: SEQ ID NO:16:

Asp Thr Glu Asp Val Val Cys Cys Ser Met Ser Tyr Lys
1               5                   10

(2) INFORMATION FOR SEQ ID NO:17:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (ix) FEATURE:
       (D) OTHER INFORMATION: /note= The aspartic acid residue at
           position 1 is biotinylated. The lysine residue at position
           13 is modified by fluorescen-5-thiolcarbamoyl.

(xi) SEQUENCE DESCRIPTION: SEQ ID NO:17:

Asp Thr Glu Asp Val Val Cys Cys Ser Met Ser Tyr Lys Lys
1               5                   10

(2) INFORMATION FOR SEQ ID NO:18:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (ix) FEATURE:
 (D) OTHER INFORMATION: /note= Xaa at position 11 is Dbu (2,3-
  diaminobutyric acid). The aspartic acid residue at
  position 1 is biotinylated. The Dbu at position 11 is
  modified by and 4,4-difluro-5,7-dimethyl-4-boro-3a,4a-
  diaza-s-indacene-3-propionyl.

(xi) SEQUENCE DESCRIPTION: SEQ ID NO:18:

Asp Thr Glu Asp Val Val Cys Cys Ser Met Xaa Tyr Arg
1               5                  10

(2) INFORMATION FOR SEQ ID NO:19:

(i) SEQUENCE CHARACTERISTICS:
  (A) LENGTH: 13 amino acids
  (B) TYPE: amino acid
  (C) STRANDEDNESS: single
  (D) TOPOLOGY: linear (ii) MOLECULE TYPE: peptide (ix) FEATURE:
 (D) OTHER INFORMATION: /note= The Xaa at position 11 is is Dbu
  (2,3-diaminobutyric acid). The aspartic acid residue at
  position 1 is biotinylated. The Dbu at position 11 is
  modified by 6-(((4-(4,4-difluro-5-(2-thienyl)-4-boro-3a,
  4a-diaza-s-indacene-3-yl) phenoxy)acetyl)amino)hexanoyl.

(xi) SEQUENCE DESCRIPTION: SEQ ID NO:19:

Asp Thr Glu Asp Val Val Cys Cys Ser Met Xaa Tyr Arg
1               5                  10

(2) INFORMATION FOR SEQ ID NO:20:

(i) SEQUENCE CHARACTERISTICS:
  (A) LENGTH: 17 amino acids
  (B) TYPE: amino acid
  (C) STRANDEDNESS: single
  (D) TOPOLOGY: linear (ii) MOLECULE TYPE: peptide (ix) FEATURE:
 (D) OTHER INFORMATION: /note= The aspartic acid residue at
  position 1 is biotinylated. The lysine residue at
  position 17 is modified by 4,4-difluro-5,7-dimethyl-4-
  boro-3a,4a-diaza-s-indacene-3-propionyl.

(xi) SEQUENCE DESCRIPTION: SEQ ID NO:20:

Asp Thr Glu Asp Val Val Cys Cys Ser Met Ser Tyr Thr Trp Thr Gly
1               5                  10                  15
Lys (2) INFORMATION FOR SEQ ID NO:21:

(i) SEQUENCE CHARACTERISTICS:
  (A) LENGTH: 17 amino acids
  (B) TYPE: amino acid
  (C) STRANDEDNESS: single
  (D) TOPOLOGY: linear (ii) MOLECULE TYPE: peptide (ix) FEATURE:
 (D) OTHER INFORMATION: /note= The aspartic acid residue at
  position 1 is biotinylated. The lysine residue at
  position 17 is modified by fluorecein-5 (or 6)-
  carboxamidoyl.

(xi) SEQUENCE DESCRIPTION: SEQ ID NO:21:

Asp Thr Glu Asp Val Val Cys Cys Ser Met Ser Tyr Thr Trp Thr Gly
1               5                   10                  15
Lys (2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 6 is Abu (a-
            aminobutyric acid). The glutamic acid residue at position
            1 is biotinylated. The amide bond between the Abu residue
            at position 6 and the alanine residue at position 7 is
            replaced with an ester bond. The lysine residue at
            position 13 is modified by fluorescein-5 (or 6)-
            carboxamidoyl.

(xi) SEQUENCE DESCRIPTION: SEQ ID NO:22:

Glu Asp Val Val Ala Xaa Ala Met Ser Tyr Thr Trp Lys
1               5                   10

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= = Xaa at position 6 is Abu (a-
            aminobutyric acid). The glutamic acid residue at position
            1 is biotinylated. The amide bond between the Abu residue
            at position 6 and the alanine residue at position 7 is
            replaced with an ester bond. The lysine residue at
            position 13 is modified by 4,4-difluro-5,7-dimethyl-4-
            boro-3a,4a-diaza-s-indacene-3-propionyl.

(xi) SEQUENCE DESCRIPTION: SEQ ID NO:23:

Glu Asp Val Val Ala Xaa Ala Met Ser Tyr Thr Trp Lys
1               5                   10

(2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: /note= Xaa at position 12 is is Abu
            (a-aminobutyric acid). The serine residue at position 1
            is biotinylated. The amide bond between the Abu residue
            at position 12 and the alanine residue at position 13 is
            replaced with an ester bond. Thelysine residue at position
            13 is replaced with an ester bond. The lysine residue at
            position 17 is modified by fluorescein-5 (or 6)-
            carboxymidoyl.

(xi) SEQUENCE DESCRIPTION: SEQ ID NO:24:

```
Ser Ser Gly Ala Asp Thr Glu Asp Val Val Ala Xaa Ala Met Ser Tyr
1               5                   10                  15
Lys
```

(2) INFORMATION FOR SEQ ID NO:25:

(i) SEQUENCE CHARACTERISTICS:
        (A) LENGTH: 638 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
Gly Arg Arg Ser Thr Ser Met Ala Pro Ile Thr Ala Tyr Ala Gln Gln
1               5                   10                  15

Thr Arg Gly Leu Leu Gly Cys Ile Ile Thr Ser Leu Thr Gly Arg Asp
            20                  25                  30

Lys Asn Gln Val Glu Gly Glu Val Gln Ile Val Ser Thr Ala Thr Gln
        35                  40                  45

Thr Phe Leu Ala Thr Cys Ile Asn Gly Val Cys Trp Thr Val Tyr His
    50                  55                  60

Gly Ala Gly Thr Arg Thr Ile Ala Ser Pro Lys Gly Pro Val Ile Gln
65                  70                  75                  80

Met Tyr Thr Asn Val Asp Gln Asp Leu Val Gly Trp Pro Ala Pro Gln
                85                  90                  95

Gly Ser Arg Ser Leu Thr Pro Cys Thr Cys Gly Ser Ser Asp Leu Tyr
            100                 105                 110

Leu Val Thr Arg His Ala Asp Val Ile Pro Val Arg Arg Arg Gly Asp
        115                 120                 125

Ser Arg Gly Ser Leu Leu Ser Pro Arg Pro Ile Ser Tyr Leu Lys Gly
    130                 135                 140

Ser Ser Gly Gly Pro Leu Leu Cys Pro Ala Gly His Ala Val Gly Leu
145                 150                 155                 160

Phe Arg Ala Ala Val Cys Thr Arg Gly Val Thr Lys Ala Val Asp Phe
                165                 170                 175

Ile Pro Val Glu Asn Leu Glu Thr Thr Met Arg Ser Pro Val Phe Thr
            180                 185                 190

Asp Asn Ser Ser Pro Pro Ala Val Pro Gln Ser Phe Gln Val Ala His
        195                 200                 205

Leu His Ala Pro Thr Gly Ser Gly Lys Ser Thr Lys Val Pro Ala Ala
    210                 215                 220

Tyr Ala Ala Gln Gly Tyr Lys Val Leu Val Leu Asn Pro Ser Val Ala
225                 230                 235                 240

Ala Thr Leu Gly Phe Gly Ala Tyr Met Ser Lys Ala His Gly Val Asp
                245                 250                 255

Pro Asn Ile Arg Thr Gly Val Arg Thr Ile Thr Thr Gly Ser Pro Ile
            260                 265                 270

Thr Tyr Ser Thr Tyr Gly Lys Phe Leu Ala Asp Gly Gly Cys Ser Gly
        275                 280                 285

Gly Ala Tyr Asp Ile Ile Cys Asp Glu Cys His Ser Thr Asp Ala
    290                 295                 300

Thr Ser Ile Leu Gly Ile Gly Thr Val Leu Asp Gln Ala Glu Thr Ala
305                 310                 315                 320

Gly Ala Arg Leu Val Val Leu Ala Thr Ala Thr Pro Pro Gly Ser Val
```

```
                        325                 330                 335
Thr Val Ser His Pro Asn Ile Glu Glu Val Ala Leu Ser Thr Thr Gly
                340                 345                 350
Glu Ile Pro Phe Tyr Gly Lys Ala Ile Pro Leu Glu Val Ile Lys Gly
                355                 360                 365
Gly Arg His Leu Ile Phe Cys His Ser Lys Lys Lys Cys Asp Glu Leu
                370                 375                 380
Ala Ala Lys Leu Val Ala Leu Gly Ile Asn Ala Val Ala Tyr Tyr Arg
385                 390                 395                 400
Gly Leu Asp Val Ser Val Ile Pro Thr Asn Gly Asp Val Val Val Val
                405                 410                 415
Ser Thr Asp Ala Leu Met Thr Gly Phe Thr Gly Asp Phe Asp Ser Val
                420                 425                 430
Ile Asp Cys Asn Thr Cys Val Thr Gln Thr Val Asp Phe Ser Leu Asp
                435                 440                 445
Pro Thr Phe Thr Ile Glu Thr Thr Thr Leu Pro Gln Asp Ala Val Ser
                450                 455                 460
Arg Thr Gln Arg Arg Gly Arg Thr Gly Arg Gly Lys Pro Gly Ile Tyr
465                 470                 475                 480
Arg Phe Val Ala Pro Gly Glu Arg Pro Ser Gly Met Phe Asp Ser Ser
                485                 490                 495
Val Leu Cys Glu Cys Tyr Asp Ala Gly Cys Ala Trp Tyr Glu Leu Met
                500                 505                 510
Pro Ala Glu Thr Thr Val Arg Leu Arg Ala Tyr Met Asn Thr Pro Gly
                515                 520                 525
Leu Pro Val Cys Gln Asp His Leu Glu Phe Trp Glu Gly Val Phe Thr
                530                 535                 540
Gly Leu Thr His Ile Asp Ala His Phe Leu Ser Gln Thr Lys Gln Ser
545                 550                 555                 560
Gly Glu Asn Phe Pro Tyr Leu Val Ala Tyr Gln Ala Thr Val Cys Ala
                565                 570                 575
Arg Ala Gln Ala Pro Pro Ser Trp Asp Gln Met Trp Lys Cys Leu
                580                 585                 590
Ile Arg Leu Lys Pro Thr Leu His Gly Pro Thr Pro Leu Leu Tyr Arg
                595                 600                 605
Leu Gly Ala Val Gln Asn Glu Val Thr Leu Thr His Pro Ile Thr Lys
                610                 615                 620
Tyr Ile Met Thr Cys Met Ser Ala Asp Leu Glu Val Val Thr
625                 630                 635

(2) INFORMATION FOR SEQ ID NO:26:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Ser Thr Trp Val Leu Val Gly Gly Val Leu Ala Ala Leu Ala Ala Tyr
1               5                   10                  15
```

```
-continued

Cys Leu Ser Thr Gly Cys Val Val Ile Val Gly Arg Ile Val Leu Ser
            20                  25                  30

Gly Lys Pro Ala Ile Ile Pro Asp Arg Glu Val Leu Tyr Gln Glu Phe
        35              40                  45

Asp Glu Met Glu Glu Cys
        50
```